United States Patent
Dube

(10) Patent No.: US 9,255,057 B2
(45) Date of Patent: Feb. 9, 2016

(54) APPARATUS AND METHOD FOR PRODUCTION OF FORMATE FROM CARBON DIOXIDE

(71) Applicant: ALSTOM TECHNOLOGY LTD, Baden (CH)

(72) Inventor: Sanjay Kumar Dube, Knoxville, TN (US)

(73) Assignee: ALSTOM Technology Ltd, Baden (CH)

( * ) Notice: Subject to any disclaimer, the term of this patent is extended or adjusted under 35 U.S.C. 154(b) by 31 days.

(21) Appl. No.: 14/252,148

(22) Filed: Apr. 14, 2014

(65) Prior Publication Data

US 2015/0291500 A1    Oct. 15, 2015

(51) Int. Cl.
    *C07C 51/41*     (2006.01)
    *B01J 19/08*     (2006.01)

(52) U.S. Cl.
    CPC ............. *C07C 51/41* (2013.01); *B01J 19/087* (2013.01); *B01J 2219/0803* (2013.01)

(58) Field of Classification Search
    CPC ........ C07C 51/41; C07C 51/15; B01J 19/087; B01J 2219/0803
    USPC .......................................................... 562/609
See application file for complete search history.

(56) References Cited

U.S. PATENT DOCUMENTS

| | | | |
|---|---|---|---|
| 5,702,570 A * | 12/1997 | Smith et al. ................. | 162/30.1 |
| 8,365,537 B2 | 2/2013 | Li et al. | |
| 8,408,006 B2 | 4/2013 | Li et al. | |
| 8,562,811 B2 | 10/2013 | Sivasankar et al. | |
| 8,592,633 B2 | 11/2013 | Cole et al. | |
| 8,641,885 B2 | 2/2014 | Sivasankar et al. | |
| 2008/0223727 A1 | 9/2008 | Oloman et al. | |
| 2011/0150733 A1* | 6/2011 | Dube et al. ............... | 423/243.06 |
| 2013/0175181 A1* | 7/2013 | Kaczur .......................... | 205/345 |

* cited by examiner

*Primary Examiner* — Jafar Parsa
*Assistant Examiner* — Amy C Bonaparte

(57) ABSTRACT

An apparatus for producing formate from carbon dioxide includes a reactor (115) that is configured to receive carbon dioxide from a separation device (109) and a first reagent to form a formate and a bicarbonate material. The bicarbonate material is sent to a regeneration device (123) that also receives a second reagent from a source of the second reagent to form the first reagent and a carbonate material. The first reagent is recycled back to the reactor (115). The carbonate material can be stored in a storage device (131) for subsequent sale or other use and/or sent to a process device (109) of a plant for processing flue gas to remove one or more acid gas elements from the flue gas by using the carbonate material received from the regeneration device (123). A method for producing formate from carbon dioxide can include use of the apparatus.

13 Claims, 2 Drawing Sheets

APPARATUS AND METHOD FOR PRODUCTION OF FORMATE FROM CARBON DIOXIDE

TECHNICAL FIELD

The present disclosure relates to an apparatus and method for producing formate from carbon dioxide.

BACKGROUND

Utility and industrial plants such as power plants, electricity generation plants, waste-to-energy facilities, cement kilns, and other facilities firing fossil fuels such as coal or oil can be configured to capture elements related to the formation of acid gases to help ensure clean and environmentally sound power generation. Such industrial plants could also include a carbon dioxide capture system to help reduce carbon dioxide emissions. The carbon dioxide capture systems can include one or more mechanisms by which the carbon dioxide is formed into a more desirable product. Examples of such carbon capture systems that can include such means for forming a product from the carbon dioxide may be appreciated from U.S. Pat. Nos. 8,365,537, 8,408,006, 8,562,811, 8,592,633, and 8,641,885 as well as U.S. Patent Application Publication No. 2008/0223727.

Operating costs and capital costs associated with operation of systems configured to reduce acid gas emissions and carbon dioxide emissions can be relatively high. The relatively high costs associated with such systems can be necessary to ensure the efficiency and effectiveness of such systems complies with air emission limits to ensure clean and environmentally sound power generation.

SUMMARY

According to aspects illustrated herein, there is provided a method for producing formate from carbon dioxide that includes the steps of: feeding carbon dioxide to a reactor, feeding a first reagent to the reactor for reacting with the carbon dioxide to produce formate and a bicarbonate material, feeding the bicarbonate material from the reactor to a regeneration device for forming a carbonate material and the first reagent, feeding a second reagent to the regeneration device for forming the carbonate material and the first reagent, recycling the first reagent from the regeneration device to the reactor for facilitating the formation of formate and the bicarbonate material, and transporting the carbonate material from the regeneration device to at least one of (i) a storage apparatus and (ii) a process device of a plant in which the carbonate material transported to the process device is to be used for processing performed by that process device.

According to other aspects illustrated herein, an apparatus for producing formate from carbon dioxide that includes an electrochemical reactor configured to receive a first reagent and carbon dioxide separated from a flue gas for forming a formate material and a bicarbonate material and a first regeneration device configured to receive the bicarbonate material from the electrochemical reactor and configured to receive a second reagent for forming the first reagent and a carbonate material. The first regeneration device can be connected to the electrochemical reactor for feeding the first reagent formed via the first regeneration device to the electrochemical reactor.

The above described and other features are exemplified by the following figures and detailed description.

BRIEF DESCRIPTION OF THE DRAWINGS

Referring now to the figures, which are exemplary embodiments, and wherein the like elements are numbered alike.

Other details, objects, and advantages of embodiments of the innovations disclosed herein will become apparent from the following description of exemplary embodiments and associated exemplary methods.

DETAILED DESCRIPTION

Disclosed herein is a plant such as a power plant, utility plant, or industrial plant, an apparatus for producing formate from carbon dioxide, and a method of practicing the same that can be configured to reduce emissions such as air pollution. Embodiments of the apparatus for producing formate from carbon dioxide can be utilized in various types of industrial facilities.

Figure 1:
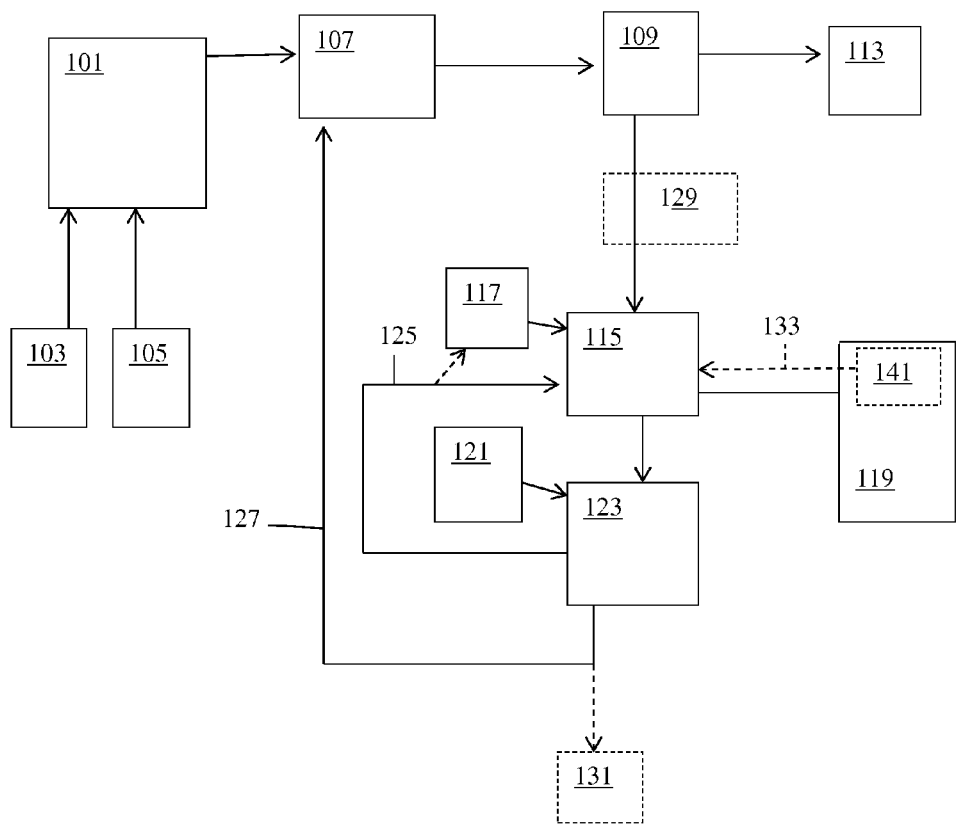
FIG. 1 is a block diagram of a first exemplary embodiment of a plant that includes an exemplary embodiment of an apparatus for producing formate from carbon dioxide.
Figure 2:
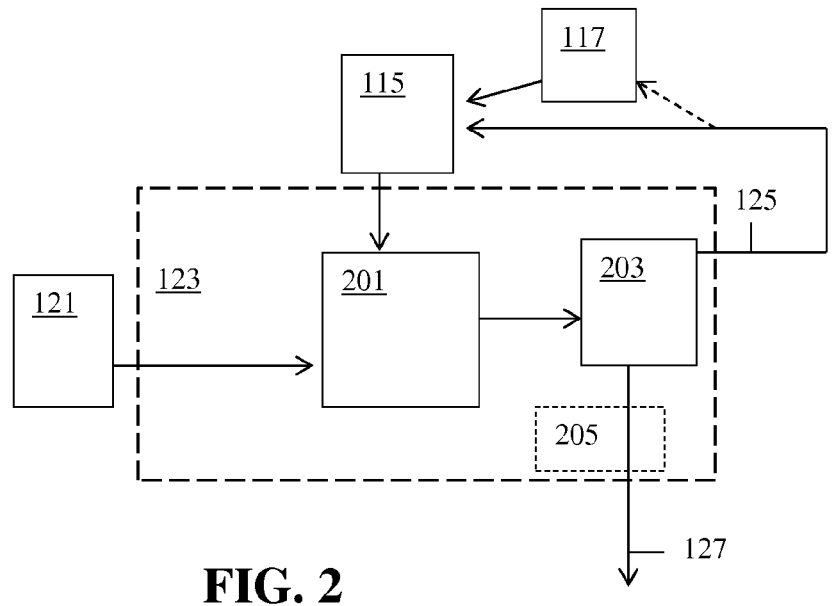
FIG. 2 is a block diagram of an exemplary apparatus for producing formate from carbon dioxide that is included within the first exemplary embodiment of the plant shown in FIG. 1.
Figure 3:
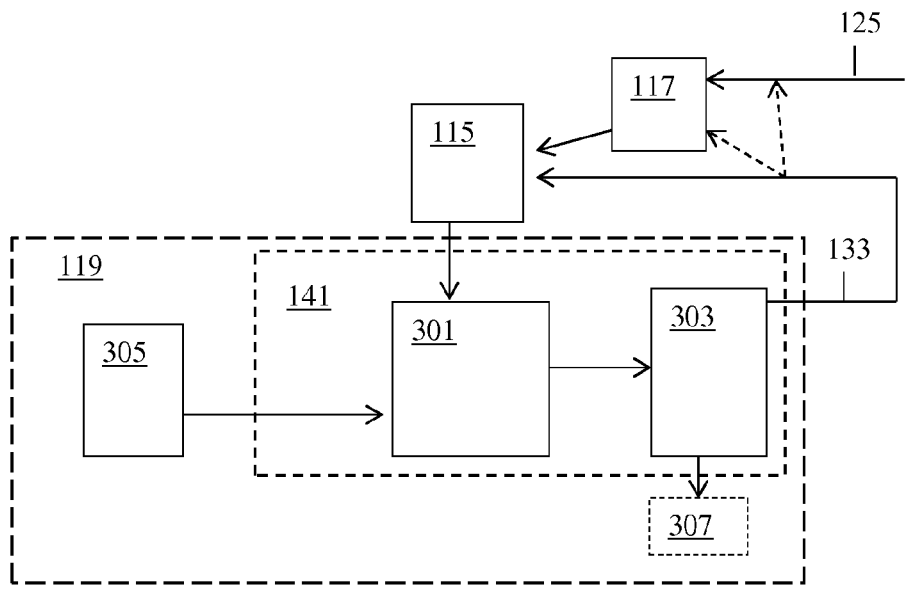
FIG. 3 is a block diagram of an exemplary apparatus for producing the first reagent from formate material output by a reactor that can be included within the first exemplary embodiment of the plant shown in FIG. 1.

Referring to FIGS. 1-3, a power plant, a utility plant or an industrial plant can include an apparatus for producing formate from carbon dioxide within the plant. The formate can be a sodium formate, potassium formate, or other formate material. The plant can include a combustor 101 that is configured to receive fuel from a source of fuel 103 for combustion of the fuel within the combustor 101. In some embodiments, the combustor can be configured as a burner, a boiler, or other type of device configured to combust a fuel into combustion products (e.g. water, carbon dioxide, etc.). The source of fuel 103 can be a storage tank, vessel, or other device configured to provide fuel to the combustor 101. The fuel can be a fossil fuel such as coal or oil. A fuel feeding conduit can connect the source of fuel 103 to the combustor 101 for feeding the fuel to the combustor 101.

The combustor 101 can also receive at least one oxidant for facilitating combustion of the fuel. The oxidant can be fed to the combustor from at least one oxidant flow source 105. The oxidant flow can be a flow of air, a substantially pure flow of oxygen from an air separation unit, or a combination of such flows of fluid. The oxidant flow can also include a portion of flue gas that was previously emitted from the combustor 101 and recycled back to the combustor 101. The one or more sources of the oxidant can be fed to the combustor via at least one oxidant conduit connected between the source of the oxidant and the combustor 101 for feeding the oxidant to the combustor 101.

The combustion of fuel in the combustor 101 can result in producing flue gas. The flue gas can be emitted from the combustor 101 and fed to a flue gas processing device 107 that is configured to remove one or more elements of acid gas from the flue gas (e.g. HCl, HF, $SO_3$, Hg, etc.). For example, the flue gas processing device 107 can include a desulfurization device such as a dry desulfurization device or a wet desulfurization device. The flue gas processing device can also include other mechanisms that are configured to remove one or more elements of acid gas from the flue gas (e.g. HCl, HF, etc.). The flue gas can be transported from the combustor 101 to the flue gas processing device 107 within a flue gas feed conduit connected between the combustor 101 and the flue gas processing device 107.

After the flue gas is treated to remove elements of acid gas from the flue gas, the flue gas can be transported from the flue gas processing device 107 to a carbon dioxide separation device 109. The treated flue gas can be transported from the flue gas processing device 107 to the carbon dioxide separation device 109 via a carbon dioxide separation device feed conduit connected between the flue gas processing device 107 and the carbon dioxide separation device 109.

A substantial portion of the carbon dioxide within the flue gas can be removed from the flue gas by the carbon dioxide separation device 109. For example, between 80-99%, of the carbon dioxide within the flue gas can be removed from the flue gas by the separation device 109 to separate that carbon dioxide from the flue gas. For instance, some embodiments can be configured such that the separation device 109 is operated to remove between 90-99% by weight of the carbon dioxide content of the flue gas. The treated flue gas having the much lower composition of carbon dioxide can be transported from the separation device 109 to a stack for emission or other device for further use. For instance, after the flue gas is treated by the separation device 109, the flue gas can be transported to a heat recovery steam generator 113 prior to being emitted out of a chimney, or stack. The heat from the flue gas can be transferred from the flue gas to one or more fluids passing through one or more heat exchangers or evaporators at least partially positioned in the heat recovery steam generator 113. A heat recovery steam generator 113 feed conduit can be connected between the heat recovery steam generator 113 and the separation device 109 for transportation of the treated flue gas from the separation device 109 to the heat recovery steam generator 113.

The carbon dioxide separated from the flue gas by the separation device 109 can be fed from the separation device 109 to an electrochemical reactor 115. The carbon dioxide from the separation device 109 can be fed to the reactor via a carbon dioxide conduit connected between the reactor 115 and the separation device 109. Water can be present with the carbon dioxide fed from the separation device 109 to the reactor 115. In addition, or an alternative, water can also be fed to the reactor 115 by one or more other sources of water (e.g. a tank, another process that is outputting water, etc.).

In some embodiments of the apparatus and in some embodiments of the plant, one or more components of a carbon dioxide treatment apparatus 129 (shown in broken line in FIG. 1) can receive the carbon dioxide from the separation device 109 prior to the carbon dioxide being fed to the reactor 115. For example, the carbon dioxide can be passed through one or more heat exchangers to be heated or cooled prior to being sent to the reactor 115. As another example, the carbon dioxide could be fed to another device prior to being sent to the reactor for further treatment or processing by the carbon dioxide treatment apparatus 129 prior to the carbon dioxide being fed to the reactor 115. For instance, the carbon dioxide can be sent to one or more compressors to increase the pressure of the carbon dioxide prior to the carbon dioxide being fed to the reactor 115.

A source of a first reagent 117 can supply a first reagent for feeding that first reagent to the reactor 115. The first reagent can be configured to facilitate a reaction with the carbon dioxide to produce a formate, or formate material, as well as bicarbonate. The first reagent can include potassium hydroxide or sodium hydroxide. It is contemplated that other types of hydroxides can also be utilized as the first reagent. The source of the first reagent can be a tank, vessel, or other mechanism that can store the first reagent or a material containing the first reagent for feeding to the reactor 115. A first reagent feed conduit can be connected between the reactor 115 and the source of the first reagent 117 so that the first reagent can be transported from the source of the first reagent 117 to the reactor 115 for use in the reactor 115.

The reactor 115 can be configured as an electrochemical reactor. The electrochemical reactor can be configured to have a cathode that receives gaseous carbon dioxide and a liquid catholyte solution as a two phase mixture at the bottom of the cathode. The liquid catholyte solution can include a formate such as a potassium formate or a sodium formate, or a bicarbonate. As the mixture travels through the cathode of the reactor 115, it contacts a catalytic tin cathode that results in the following reactions occurring:

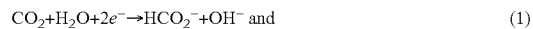  (1)

  (2)

Reaction (1) results in carbon dioxide being produced into formate ($HCO_2^-$). Reaction (2) results in the reduction of water to hydrogen gas and hydroxide.

In the anode chamber of the reactor, the first reagent can be introduced such that an anolyte of the first reagent can be present therein so that the following oxidation reaction occurs: (3) $2OH^- \rightarrow \tfrac{1}{2}O_2 + H_2O + 2e^-$. In the event the first reagent is potassium hydroxide, potassium ions migrate across a selectively permeable membrane to balance the charge across the reactor 115. If sodium hydroxide is used as the first reagent, sodium ions migrate across the permeable member to balance the charge across the reactor 115. In the event the first reagent is another type of alkali salt such as calcium hydroxide or magnesium hydroxide, then calcium or magnesium ions would migrate across the membrane.

The reactor can operate at a preselected pH range, such as a pH range of 7.5-9.0. The hydroxide ions can be at a low concentration, but at a sufficient strength to further react with carbon dioxide to form bicarbonate in the reactor 115 through the following reaction (4): $CO_2OH^{--} \rightarrow HCO_3^-$. The combination of reactions (1) and (2) with (4) can result in the production of other materials. For instance, when the first reagent is potassium hydroxide, the following reactions can occur in the reactor 115:

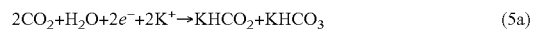  (5a)

  (6a)

As another example, when the first reagent is sodium hydroxide, the following reactions can occur in the reactor 115:

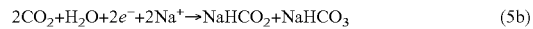  (5b)

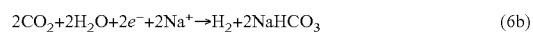  (6b)

Reactions (5a) and (6a) or reactions (5b) and (6b) can serve as a basis of operation for the cathode and Reaction (3) can provide the basis of operation of the anode of the electrochemical reactor 115. The cathode side of the reactor 115 can be plated with tin or a tin-lead alloy to help suppress the decomposition of water to hydrogen (Reaction (2)). Such a coating can also help protect the cathode against corrosion.

The formate or formate material produced in the reactor can be output from the reactor 115 and transported to another plant mechanism 119 for further processing (e.g. storage, product purification, etc.) via a formate transport conduit connected between the rector 115 and the plant mechanism 119. The plant mechanism can be a storage tank, vessel, or other mechanism for storing formate until that formate is needed for resale, distribution, or other processing. The plant mechanism 119 can also, or alternatively, include a regeneration system that is configured to regenerate the first reagent from the formate material for recycling the first reagent back to the reactor 115 via a recycle conduit 133 connected between the regenerator of the plant mechanism 119 and the reactor 115.

Operation of the reactor 115 can result in a substantial production of formate as well as bicarbonate. For instance, for every mole of formate material produced by the reactor 115, a mole of bicarbonate material may also be produced by the reactor 115. Bicarbonate could be considered an undesirable output for many industrial plant, power plant, or utility plant operators. But, it has been determined that it would be desirable to utilize the bicarbonate to help reduce operating costs associated with the first reagent being fed to the reactor 115 from a source of the first reagent 117 via a first reagent feed conduit connected between the source of the first reagent 117 and the reactor 115 so that the first reagent can be regenerated for recycling back to the reactor 115 so that less new first reagent material is needed for feeding to the reactor 115 for forming formate. It has been determined that such an arrangement can help drastically reduce operational costs associated with the production of formate.

The bicarbonate, or bicarbonate material (e.g. material containing the bicarbonate produced in the reactor 115), formed in the reactor 115 can be output from the reactor 115 and sent to a first regeneration device 123. The first regeneration device 123 can be configured to utilize the bicarbonate to form the first reagent for sending back to the reactor 115. The bicarbonate can be transported from the reactor 115 to the first regeneration device 123 via a bicarbonate transport conduit connected between the reactor 115 and first regeneration device 123 so that bicarbonate is fed to the first regeneration device 123 for use in forming the first reagent.

The first regeneration device 123 also receives a second reagent from a source of the second reagent 121. A second reagent feed conduit connected between the source of the second reagent 121 and the first regeneration device 123 can transport the second reagent or a material comprising the second reagent to the first regeneration device 123 for reacting with the bicarbonate from the reactor 115 to form the first reagent. The second reagent can be a material that reacts with bicarbonate to form the first reagent. For example, the second reagent can be comprised of lime (CaO), which is also known as calcium oxide. In some embodiments, the lime could be a slaked lime.

The first regeneration device 123 can have a number of different configurations. In one embodiment, the first regeneration device 123 includes at least one tank 201. The tank 201 is connected to the second reagent feed conduit for receiving the second reagent from the source of the second reagent 121. The tank 201 is also connected to the bicarbonate transport conduit so that the tank receives bicarbonate output from the reactor 115. The tank 201 can include an agitation mechanism or other mechanisms to help facilitate the mixing of the second reagent with the bicarbonate material within the tank for a preselected residence time so that the second reagent and the bicarbonate material react to form the first reagent and a carbonate material (e.g. calcium carbonate, sodium carbonate, potassium carbonate, etc.).

When the second reagent material is lime (CaO), the bicarbonate may react with the second reagent to form the first reagent (e.g. NaOH or KOH) and calcium carbonate ($CaCO_3$) as the carbonate material. The mixture containing the calcium carbonate and first reagent can be fed from the tank 201 to at least one cyclone 203 after the bicarbonate and second reagent were retained within the tank 201 for a preselected residence time to react with each other to produce the calcium carbonate and first reagent. Each cyclone can be a hydrocyclone or other types of cyclone. The at least one cyclone 203 can include just one cyclone or multiple cyclones. When multiple cyclones are utilized, the cyclones can be arranged in series or may each be configured to receive a selected portion of the first reagent and calcium carbonate to separate those materials from each other. A cyclone feed conduit can be connected between each cyclone 203 and the tank 201 for transporting the carbonate material and first reagent to the at least one cyclone 203 for separation and subsequent outputting of those materials.

The carbonate material separated from the first reagent by the at least one cyclone 203 can be output from the at least one cyclone to a carbonate material transportation conduit 127 connected between the cyclone and the flue gas processing device 107 for feeding the carbonate material to the flue gas processing device for use in processing flue gas passing through the flue gas processing device 107. One or more filtration devices 205 (shown in broken line in FIG. 2) can be positioned for receiving the carbonate material flow from each cyclone 203 to dewater the carbonate material if needed for further use of the carbonate material flow. For example, when calcium carbonate is the carbonate material, the calcium carbonate can be sent to a filtration device 205 and then be subsequently sent to a desulfurization device embodiment of the flue gas processing device 107 for being contacted with the flue gas for absorbing acid gas elements from the flue gas for removing acid gas components from the flue gas passing through the flue gas processing device 107. Use of the carbonate material in flue gas processing performed by the flue gas processing device 107 can reduce operating costs of the plant or flue gas processing device 107 as a lower amount of "new" material can be needed by that device for treating the flue gas.

In addition, or as an alternative, the carbonate material can be fed to a carbonate material storage apparatus 131 via a portion of the carbonate material transportation conduit 127 connected between the at least one cyclone 203 and the storage apparatus 131. A valve or other distribution device of the carbonate material transportation conduit 127 can be moved or adjusted to distribute the carbonate material that is sent to such storage apparatus 131 as compared to the amount of such material sent to a flue gas processing device 107 for use in treating or otherwise processing the flue gas passing therethrough. As yet another alternative, some embodiments of the apparatus can be configured so that all the carbonate material may always be sent to the storage apparatus 131 via the carbonate material transportation conduit 127 so that no carbonate material is sent to a flue gas processing device 107.

The first reagent material separated by the at least one cyclone 203 can be recycled to the reactor 115 via a first reagent recycle conduit 125 connected between the at least one cyclone 203 and the reactor 115 so that first reagent can be fed to the reactor 115 via the first recycle conduit 125. The recycling of the first reagent via the first reagent recycle conduit 125 can permit operations of the first reactor 115 to require less "new" first reagent to be utilized from the source of the first reagent 117, which can reduce operating costs associated with operations of the reactor 115. Further, the recycling of the first reagent produced by the first regeneration device 123 via the first reagent recycle conduit 125 can help reduce capital costs associated with the plant or an apparatus for forming formate from carbon dioxide by reducing the need for devices that can be necessary to process a material containing a first reagent for feeding to a reactor 115 (e.g. transportation and storage costs associated with the first reagent, tanks, pumps, piping, classifiers, etc.). For instance, it is contemplated that there may only be a need for a relatively small amount of "new" first reagent material from the source of the first reagent material 117 once the apparatus is at steady state operations such that the size of devices for processing the first reagent for feeding to the reactor 115 can be substantially smaller and less expensive. For instance, about 50% of the first reagent utilized in the reactor 115 can be recovered by use of the first regenerator device 123 in embodiments of the plant and apparatus, which can provide a substantial operational costs savings and reduce the need for new first reagent that must be obtained from a supplier for continued operations of the reactor 115.

Depending on the production of the first reagent provided by the first regeneration device 123 and the rate at which the reactor 115 is producing formate material and bicarbonate material, the produced first reagent can be fed to the source of the first reagent or other first reagent storing device for storage prior to being fed back to the reactor 115. A valve can be configured in the first reagent recycle conduit 125 to adjustably distribute a flow of the first reagent from the regeneration device 123 so that some portion of the first reagent is fed to the source of the first reagent 117 for storage and another portion of the first reagent is recycled back to the reactor 115, as indicated in broken line in FIG. 1. The valve or other distribution mechanism of the conduit can be adjusted from a first position in which all of the first reagent is recycled back to the reactor 115 to a second position in which all the first reagent is distributed to the source for the first reagent 117 for storage within a tank or other vessel in which the first reagent can be stored prior to being recycled back to the reactor 115 via the first reagent feed conduit connecting the source of the first reagent 117 to the reactor 115.

In addition, formate material produced in the reactor 115 can be fed to a system for regenerating the first reagent from the formate for recycling the first reagent back to the reactor 115. For example, formate material output from the reactor 115 can be fed to a plant mechanism 119 that includes a second regeneration device 141 (shown in broken line in FIG. 1) that is configured to regenerate first reagent material from the formate material received from the reactor 115 for recycling that first reagent material back to the reactor 115 via a first reagent recycle conduit 133 connected between the second regeneration device 141 and the reactor 115.

As can be appreciated from FIG. 3, the second regeneration device 141 can be configured to receive a third reagent from a source of the third reagent 305. The third reagent can be transported from the source of the third reagent 305 a tank 301 of the second regeneration device 141 via a third reagent feed conduit connected between the source of the third reagent and the tank 301. The tank 301 can also receive formate material from the reactor 115 via a formate material transport conduit connected between the second regeneration device 141 and the reactor 115. The tank 301 can be configured to mix the formate material with the third reagent and can also be configured to heat or otherwise affect the mixture to help facilitate a reaction of the third reagent with the formate material received from the reactor 115. For example, the tank 301 can include an agitation mechanism or other mixing mechanism to help facilitate the mixing of the formate and the third reagent. The tank can also be sized or otherwise configured so that the third reagent and formate material are retained within the tank for a preselected residence time period.

The third reagent can be configured to react with the formate material to produce the first reagent as well as one or more other compounds when mixed with the formate material within the tank 301. For example, the third reagent can be sodium hydroxide when the first reagent is potassium hydroxide. The sodium hydroxide can react with the potassium formate material to form potassium hydroxide and sodium formate (e.g. reaction (7) of $KHCO_2 + NaOH \rightarrow NAHCO_2 + KOH$ can occur within the tank 301 when the first reagent is potassium hydroxide and the third reagent is sodium hydroxide). The first reagent and the one or more other compounds formed by use of the third reagent within the tank 301 can be output to a first reagent separation device 303 by a conduit connected between the tank 301 and first reagent separation device 303. The first reagent separation device 303 can be one or more cyclones of other type of separation device that is configured separate the first reagent from the one or more other compounds so that the first reagent is recycled back to the reactor 115 via the first reagent recycle conduit 133 connected between the first reagent separation device 303 and the reactor 115 and/or the source of the first reagent 117. For example, the first reagent can be transported directly to the reactor 115 to recycle the first reagent back to the reactor 115. As another example, the first reagent can be transported to the source of the first reagent 117 for being temporarily retained by the source of the first reagent 117 prior to being sent to the reactor 115 for recycling the first reagent from the second regeneration device 141 to the reactor 115 as indicated by the broken line arrow shown in FIG. 3. For instance, the first reagent from the first reagent separation device 303 can be merged with the first reagent from the first reagent conduit 125 of the first regeneration device for merging the flows of the first reagent for transportation to the source of the first reagent 117 for recycling the first reagent to the reactor 115 or the recycled first reagent flows from the first and second regeneration devices 123 and 141 can be fed to the source of the first reagent 117 without merging of the flows via totally separate paths defined by different conduits.

The one or more other compounds separated from the first reagent by the first reagent separation device 303 can be output to a processing device 307 or other mechanism for further processing and/or storage of those materials by an output conduit connected between the first reagent separation device 303 and the processing device 307. For instance, when sodium formate is formed as the other compound, the sodium formate can be sent to a processing device 307 for purification of the sodium formate prior to storage and subsequent distribution of the sodium formate.

It has been determined that embodiments of the apparatus for production of formate from carbon dioxide can provide operating and capital cost reductions compared to other systems for producing formate. For instance, by using a second reagent of a low cost relative to the cost of the first reagent (e.g. use of lime as a second reagent that has a lower cost as compared to the cost of the first reagent) for forming a carbonate material and the first reagent, substantial cost savings can be achieved as compared to no formation of a first reagent by use of the formed bicarbonate material and a second reagent for forming the first reagent for recycling back into use as well as forming calcium oxide that can be used in other plant processing. For example, an operational cost savings of between 20-170 million Euros can be provided by use of a second reagent of a lower cost such as lime to form the first reagent from bicarbonate formed by the reactor as compared to utilizing only "new" sodium hydroxide for feeding to the reactor for operations of the reactor for different sized plants. As another example, an operational cost savings of between 20 million Euros and 1.2 billion Euros can be provided by use of a second reagent of a lower cost such as lime to form the first reagent from bicarbonate formed by the reactor for recycling to the reactor as compared to using only "new" potassium hydroxide for feeding to the reactor. The above noted ranges of savings are based on an estimated plant life of 25 years. The smaller savings value for each range is a projection for a smaller sized plant whereas the larger end of the savings range is for a plant or a larger size.

The operational and capital cost savings can be further increased by use of a plant a second regeneration device 141 to regenerate the first reagent from the formate material produced by the reactor 115 to recycle the regenerated first reagent to the reactor 115. For example, as much as 50% of the first reagent used in the reactor 115 can be regenerated from use of the first regeneration device 123. As much as 50% of the first reagent can also be recovered and recycled to the reactor 115 by use of the second regeneration device 141. Use of both the first and second regeneration devices 123 and 141 can therefore theoretically recycle up to 100% of the first reagent used in the reactor 115. That being said, it is contemplated that the amount of first reagent recycled by the use of the first and second regeneration devices 123 and 141 will be between be 80-95% or 90-95% of the first reagent utilized in the reactor 115 due to practical limitations and costs considerations associated with operation of the plant.

Further, use of the first and second regeneration devices 123 and 141 can reduce the need for time and expense associated with development of different reactors for use with different reagents as only one reagent can be needed for operations of the reactor 115 so that sizing of the entire reactor 115 can be developed just for one single reagent (e.g. the first reagent). If a different reagent formate is needed to be an output by the reactor 115 for other purposes (e.g. use of that formate in other plant processes, etc.) for a particular customer, then the other formate can be produced outside of the reactor 115 by using the second regeneration device 141 so that development of bids and bids on projects can be accomplished by a supplier more quickly and accurately.

It should be appreciated that various changes can be made to embodiments of the apparatus for integrating an apparatus for formate production from carbon dioxide within a plant to account for different design criteria. For example, the size, shape or configuration of conduits for transporting different fluids or materials to and from different elements of the apparatus can be any of a number of suitable shapes, sizes, or configurations and include any of a number of different conduit elements such as vessels, valves, pipes, tubes, tanks, or ducts that have the flow rate of fluid affected by pumps, fans or fluid flow control mechanisms connected to or in fluid communication with such elements. Each conduit could also be considered a section of a larger system of conduits or be considered sections of a solitary conduit system used to transport fluids throughout a plant. As another example, the temperatures and/or pressures at which the flue gas, first reagent, second reagent, carbon dioxide flows, formate flow, carbonate material flow or other fluid flows are to be maintained at or kept can also be any of a number of suitable ranges to meet a particular set of design objectives. As another example, the types of pumps, fans, or other mechanisms used to control or drive fluid flows throughout the apparatus can be any arrangement of such mechanisms that can meet a particular set of design criteria. As yet another example, embodiments of the apparatus for producing formate from carbon dioxide can be configured to utilize one or more devices of the apparatus (e.g. utilize one or more regenerators 123, tanks 201, cyclones, sources of reagents, carbon dioxide separators, flue gas processing devices, etc.) and one or more conduits utilized for transporting fluid between those devices. As yet another example, the third reagent can be any type of reagent suitable for forming the first reagent from the formate material (e.g. potassium hydroxide, sodium hydroxide, etc.). Additionally, an arrangement of sensors, one or more controllers, and other automated process control mechanisms can be included in the plant and/or apparatus for producing formate from carbon dioxide to meet a particular set of design criteria for monitoring and controlling operations of the plant or apparatus or at least one device of the plant or apparatus.

While the invention has been described with reference to various exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of producing formate from carbon dioxide, comprising:
   feeding carbon dioxide to a cathode of an electrochemical reactor;
   feeding a first reagent to the reactor to an anode of the electrochemical reactor;
   operating the reactor to generate formate and a bicarbonate salt;
   collecting the formate;
   feeding the bicarbonate salt from the electrochemical reactor to a regeneration device;
   feeding a second reagent to the regeneration device for reacting with the bicarbonate salt and forming a carbonate salt and the first reagent;
   recycling the first reagent from the regeneration device to the anode of the electrochemical reactor for facilitating the formation of formate and the bicarbonate salt; and
   transporting the carbonate salt from the regeneration device to at least one of (i) a storage apparatus and (ii) a process device of a plant in which the carbonate salt transported to the process device is to be used for processing performed by that process device.

2. The method of claim 1, wherein the first reagent comprises one of sodium hydroxide (NaOH) and potassium hydroxide (KOH); and
   the formate comprises one of potassium formate (KHCOO) and sodium formate (NaHCOO).

3. The method of claim 2, wherein the bicarbonate salt comprises one of sodium bicarbonate (NaHCO3) and potassium bicarbonate (KHCO3).

4. The method of claim 1, wherein the second reagent comprises lime (CaO).

5. The method of claim 4, wherein the carbonate salt comprises calcium carbonate (CaCO3).

6. The method of claim 1, wherein the reactor is an electrochemical reactor and the carbonate salt is transported to the process device of the plant.

7. The method of claim 6, wherein the process device of the plant is a desulfurization device, the method comprising:
   the desulfurization device receiving a flue gas and the carbonate salt for removing a portion of at least one acid gas element from the flue gas.

8. The method of claim 7, comprising:
   feeding flue gas formed from combustion of a fuel to a separation device of the plant to separate carbon dioxide from the flue gas; and wherein the carbon dioxide fed to the reactor is the carbon dioxide separated from the flue gas by the separation device.

9. A method for producing formate from carbon dioxide comprising:
   feeding carbon dioxide to a cathode of an electrochemical reactor;
   feeding sodium hydroxide or potassium hydroxide to an anode of the electrochemical reactor;
   operating the reactor to generate one of: (i) potassium formate and potassium bicarbonate and (ii) sodium formate and sodium bicarbonate;
   collecting the potassium formate or the sodium formate;
   feeding the sodium bicarbonate or the potassium bicarbonate from the electrochemical reactor to a regeneration device;
   feeding lime to the regeneration device for reacting with the sodium bicarbonate or the potassium bicarbonate to form a carbonate salt and sodium hydroxide or potassium hydroxide;
   recycling the sodium hydroxide or the potassium hydroxide from the regeneration device to the anode of the electrochemical reactor for facilitating the formation of the one of (i) the potassium formate and potassium bicarbonate and (ii) the sodium formate and sodium bicarbonate that occurs via the operating of the reactor; and
   transporting the carbonate salt from the regeneration device to at least one of (i) a storage apparatus and (ii) a process device of a plant in which the carbonate salt transported to the process device is to be used for processing performed by that process device.

10. The method of claim 9, wherein the carbonate salt comprises calcium carbonate.

11. The method of claim 9, wherein the reactor is an electrochemical reactor and the carbonate salt is transported to the process device of the plant.

12. The method of claim 11, wherein the process device of the plant is a desulfurization device, the method comprising:
   the desulfurization device receiving a flue gas and the carbonate salt for removing a portion of at least one acid gas element from the flue gas.

13. The method of claim 12, comprising:
   feeding flue gas formed from combustion of a fuel to a separation device of the plant to separate carbon dioxide from the flue gas; and
   wherein the carbon dioxide fed to the reactor is the carbon dioxide separated from the flue gas by the separation device.

* * * * *